United States Patent [19]

Hsien-fen Kuh Lai et al.

[11] Patent Number: 5,525,496
[45] Date of Patent: Jun. 11, 1996

[54] DNA SEQUENCE ENCODING STEROL Δ14 REDUCTASE

[75] Inventors: Margaret Hsien-fen Kuh Lai, E. Brunswick; Donald R. Kirsch, Princeton, both of N.J.; Martin Bard, Carmel, Ind.

[73] Assignee: American Cyanamid Company, Wayne, N.J.

[21] Appl. No.: 440,674

[22] Filed: May 15, 1995

Related U.S. Application Data

[62] Division of Ser. No. 107,347, Aug. 16, 1993, abandoned.

[51] Int. Cl.[6] ............ C12N 9/02; C12N 15/53; C12N 15/81; A61K 38/44
[52] U.S. Cl. ............ 435/189; 435/69.1; 435/252.3; 435/320.1; 514/2; 536/23.2; 935/14; 935/29; 935/69; 935/73
[58] Field of Search ............ 435/189; 536/23.2

[56] References Cited

PUBLICATIONS

Ashman, W. H., et al., Lipids 26: 628–632 (1991).
Baloch, R. and Mercer, I., Phytochemistry 26: 663–668 (1987).
Balzi, E., et al., J. Biol. Chem. 262: 16871–16879 (1987).
Brugge, J. S., et al., Mol. Cell. Biol. 7: 2180–2187 (1987).
Chen, W., et al., Yeast 7: 305–308 (1991).
Gaber, R. F., et al., Mol. Cell. Biol. 9: 3447–3456 (1989).
Kyte, J., and Doolittle, R. F., J. Mol. Biol. 157: 105–132 (1982).
Lorenz, T., and Parks, L. W., DNA and Cell Biol. 11: 685–692 (1992).
Marcireau, C., et al, Curr. Genet. 22: 267–272 (1992).
Molzahn, S. W., and Woods, R. A., J. Gen Microbiol. 72: 339–348 (1972).
Nasmyth, K. A., and Tatchell, K., Cell 19: 753–764 (1980).
Paltauf, F., et al., in Jones, E. W., et al., eds., The Molecular and Cellular Biology of the Yast Saccharomyces, Gene Expression, Cold Spring Harbor Laboratory Press, 1992, pp. 415, 418–420, 424–428, and 434–437.
Shimanauki, M., et al., Mol. Biol. Cell 3: 263–273 (1992).
Worman, H. J., et al., J. Cell Biology 111: 1535–1542 (1990).

*Primary Examiner*—Charles L. Patterson, Jr.
*Assistant Examiner*—William W. Moore
*Attorney, Agent, or Firm*—Darryl L. Webster; Mary M. Krinsky

[57] ABSTRACT

A gene encoding *Saccharomyces cerevisiae* sterol Δ14 reductase of the ergosterol biosynthetic pathway is isolated and cloned by selecting strains carrying sequences on a 2μ based vector for resistance to a morpholine fungicide such as fenpropimorph. Four distinct plasmid inserts which produce morpholine resistance are obtained, and one of these is characterized and sequenced. The purified and isolated DNA sequence encoding sterol Δ14 reductase encodes a polypeptide exhibiting homology to the *S. cerevisiae* sterol C-24(28) reductase enzyme in the ergosterol biosynthetic pathway.

4 Claims, 4 Drawing Sheets

PML100
LAMBR
YGL022
ST SL

| | | | | | | | | | | | | | | | | | | | | | | |
|---|---|---|---|---|---|---|---|---|---|---|---|---|---|---|---|---|---|---|---|---|---|---|
|PML100|N|P|R|T|T|E|F|E|F|G|G|L|I|G|A|L|G|I|S|I|G|L|P|V|F|T|I|I|L|
|LAMBR|S|S|K|T|K|E|L|E|F|G|G|R|F|G|T|F|M|L|M|F|F|L|P|A|T|V|L|Y|L|
|YGL022|K|P|N|E|I|E|Y|E|F|G|G|T|T|G|V|I|G|M|L|I|G|F|P|L|L|M|Y|Y|M|
|ST SL|V|K|K|S|A|P|R|E|F|G|G|A|K|G|A|L|A|I|M|T|G|F|P|C|L|M|Y|Y|L|

PML100  K P L R Y Y L G N R E L W T V Y C L W Y G I L A V L D V I
LAMBR   L P A L E S L W E T K V F G V F L L W F F F Q A L F Y L L
YGL022  L V L E N G I P E K Y D W T I F L T F W V F Q I I F Y Y T
ST SL   Y I Y V G A Y P T R Y A F L V F W S F C I V Q A V M Y L T

PML100  L V L A I R W K L T D G Q L P E L Q Y L Y E N H V S L C I
LAMBR   L T A A A I Q T L L Y F Q F - E L H Y L Y D H F V Q F A V
YGL022  L Y V T T T L V L V L H F T N L F R L Y V I I D R F G R I
ST SL   F Y T T I V I L A V L H V T H V F P I T T F I D M F G P L

PML100  E K I L A L G G N S G N I I Y D W F I G R E L N P R L G P
LAMBR   E E D L A P G G N S G Y L V Y N F F T G H E L N P R I G S
YGL022  F I S H D Y H R M T G N H L Y D F F M G A P L N P R W G I
ST SL   R L F D K P H R L S G N P I Y D A F M G A C L N P R L G K

PML100  K T G K I N D A L V L V N F L Q G F Y I F D G V L N E E G
LAMBR   N Q S M P S L S M I L V N S F Q L L Y V V D A L W N E E A
YGL022  T Y G Y V T P Q L G V V M L A H W L Y A N A C A K G E E L
ST SL   T Y G T V S P Q V L F V C L G H Y L Y A N A C S K G E Q L

PML100  A R Y L S V S P V E L G W V K V V G - - - I L A I M F L G
LAMBR   A F Y I V G H P I A I S W P V A A A - - - I T I L N C I G
YGL022  T L Y L Y Y H D P S E Y H W S T L Y N V S L Y V V L L C A
ST SL   T L Y L F S H D P S V Y N W S T Q Y T T G I Y V L L L C C

PML100  Q G K L E N L K S I Q T K R G T K L L C D G W W A K S Q
LAMBR   A D P K L S Y L K V I P T A T G K G L L V T G W W G F V R
YGL022  P Y Q I L K N P K Y M V T S N G S Y L L I D G W Y T L A R
ST SL   P W L I I K N P T F I R C A N G G T L L T S G W Y R Y A R

PML100  F A T L L L H R Q Q R D E H K C R L K Y G E N W E E Y E R
LAMBR   E I C L L V H R E A R D E H H C K K K Y G L A W E R Y C Q
YGL022  I L V V L I H R A F R D Q A K C K R K Y G K D W D E Y C K
ST SL   I F V V L V H R V S R D I K K C K A K Y G A D F D E Y D R

DNA SEQUENCE ENCODING STEROL Δ14 REDUCTASE

This is a continuation of application Ser. No. 08/107,347 filed on Aug. 16, 1993, now abandoned.

TECHNICAL FIELD OF THE INVENTION

This invention relates to the identification of a *Saccharomyces cerevisiae* gene encoding sterol Δ14 reductase.

BACKGROUND OF THE INVENTION

Sterols are steroid alcohols of vegetable and animal origin. Ergosterol is the principal membrane sterol of fungi. It is structurally similar to its animal counterpart, cholesterol, and its higher plant counterparts, stigmasterol and sitosterol. Though the biosynthesis of ergosterol in fungi involves steps distinct from the other sterols, the pathways in different organisms share several common steps. The lanosterol 14α-demethylation steps in cholesterol and ergosterol formation in animals and fungi, as well as the obtusifoliol 14Δ-demethylation in stigmasterol and sitosterol biosynthesis in plants, both lead to the formation of a double bond between carbons 14 and 15 of the sterol ring. This double bond is then reduced by sterol Δ14 reductase activity. The enzyme is located in the microsomal fraction in pig liver, yeast and Zea mays, and requires NADPH as an electron donor (Marcireau, C., et al., *Curr. Genet.* 22: 267–272 (1992)).

Genetic studies of ergosterol biosynthesis mainly have been carried out in *Saccharomyces cerevisiae* (Paltauf, F., et al., in Jones, E. W., et al., eds., *The Molecular and Cellular Biology of the Yeast Saccharomyces, Gene Expression*, Cold Spring Harbor Laboratory Press, 1992, pages 434–437). In yeast, ergosterol affects membrane fluidity and permeability and plays an essential role in the yeast cell cycle.

A number of mutations in the yeast ergosterol biosynthetic pathway have been isolated either by reverse genetic approaches or by selection for mutations producing polyene resistance, and many of the genes have been identified. Toward the end of the pathway, sterol Δ14 reductase, Δ8–Δ7 isomerase, and C-24(28) reductase catalyze steps in the conversion of lanosterol to ergosterol. After ignosterol is reduced by sterol Δ14 reductase, which eliminates a double bond in the D ring of the molecule, the sterol is demethylated and rearranged to fecosterol, which is then isomerized by sterol Δ8–Δ7 isomerase. The sterol is then desaturated in two positions and its side chain is reduced by C-24(28) reductase. Some of the genes encoding the enzymes have been identified and named as follows (Paultauf, et al., cited above, Lorenz, T., and Parks, L. W., *DNA and Cell Biol.* 11: 685–692 (1992), and Example 1 below):

| Enzyme | Gene |
| --- | --- |
| Δ14 reductase | ERG24 |
| C-24 methyl transferase | ERG6 |
| Δ8 - Δ7 isomerase | ERG2 |
| C-24(28) reductase | ERG4 |

Based on the accumulation of intermediates following fungicide treatment, morpholine fungicidal compounds such as tridemorph and fenpropimorph have been reported to be inhibitors of sterol 14 reductase and sterol Δ8–Δ7 isomerase (Baloch, R. and Mercer, I., *Phytochemistry* 26: 663–668 (1987)). However, it recently has been found that the sterol Δ8–Δ7 isomerase gene is not essential for viability in *S. cerevisiae* (Ashman, W. H., et al., *Lipids* 26: 628–632 (1991)), suggesting that the killing effect of morpholine fungicides may be primarily the result of sterol Δ14 reductase inhibition.

It has also been shown that the C-24 methyl transferase gene (ERG6) is not essential for viability in *S. cerevisiae* (Gaber, R. F., et al., *Mol. Cell. Biol.* 9: 3447–3456 (1989)). Mutant cells exhibit normal vegetative growth, but they differ from the wildtype in a number of respects, including drug supersensitivity, presumably due to alterations in membrane function (ibid.). Drug super-sensitivity has been observed in other yeast mutants, including one denoted YGL022 which encodes a putative transport protein (Chen, W., et al., *Yeast* 7: 305–308 (1991)).

SUMMARY OF THE INVENTION

The objects of the invention are to identify a gene encoding sterol Δ14 reductase, to elucidate the primary structure of the enzyme encoded by the gene, and to investigate the relationship of the structure to other polypeptides, especially other enzymes in the sterol biosynthetic pathway. The sterol Δ14 reductase gene and enzyme are useful in devising screening tests to identify sterol biosynthesis inhibitors that are potential fungicides for a wide variety of agricultural, medical, and veterinary applications.

These and other objects are accomplished by the present invention, which provides a gene encoding sterol Δ14 reductase, the polypeptide primary structure it encodes, and the relationship of the structure to other polypeptides. Also provided are RNA sequences corresponding to the DNA sequence of the gene, biologically functional plasmids or vectors comprising the DNA or RNA sequence, and procaryotic or eucaryotic host cells transformed or transfected with the plasmid or vector in a manner allowing the host cell to express the polypeptide.

A DNA sequence encoding *Saccharomyces cerevisiae* sterol Δ14 reductase is cloned by selecting strains carrying sequences on a 2μ based vector for resistance to a morpholine fungicide such as fenpropimorph, fenpropidin, or tridimorph. Fenpropimorph is preferred. When fenpropimorph is employed, four distinct plasmid inserts which produce morpholine resistance are obtained, denoted pML99, pML100, pML101 and pML103, which are useful in screens of sterol biosynthesis inhibition. One of these, pML100, is characterized and sequenced, and the putative amino acid sequence of the polypeptide encoded by the open reading frame is determined (SEQ ID NO 1).

DESCRIPTION OF THE FIGURES

FIG. 3 depicts a comparison of the amino acid sequence derived from the major open reading frame of the pML100 sequence encoding *S. cerevisiae* sterol Δ14 reductase (SEQ ID NO 1) with three homologous sequences: the chicken nuclear lamin B receptor (SEQ ID NO 2, Worman, H. J., et al., *J. Cell Biology* 111: 1535–1542 (1990)), the *Saccharomyces cerevisiae* YGL022 sequence (SEQ ID NO 3, Chen, et al., cited above), and the *Schizosaccharomyces pombe* stsl gene (SEQ ID NO 4, Shimanuki, M., et al., *Mol. Biol. Cell* 3: 263–273 (1992)). The figure employs standard one-letter nomenclature for the amino acids: A, Ala; C, Cys; D, Asp; E, Glu; F, Phe; G, Gly; H, His; I, Ile; K, Lys; L, Leu; M, Met; N, Asn; P, Pro; Q, Gln; R, Arg; S, Ser; T, Thr; V, Val; W, Trp; and Y, Tyr.

DETAILED DESCRIPTION OF THE INVENTION

Figure 1:
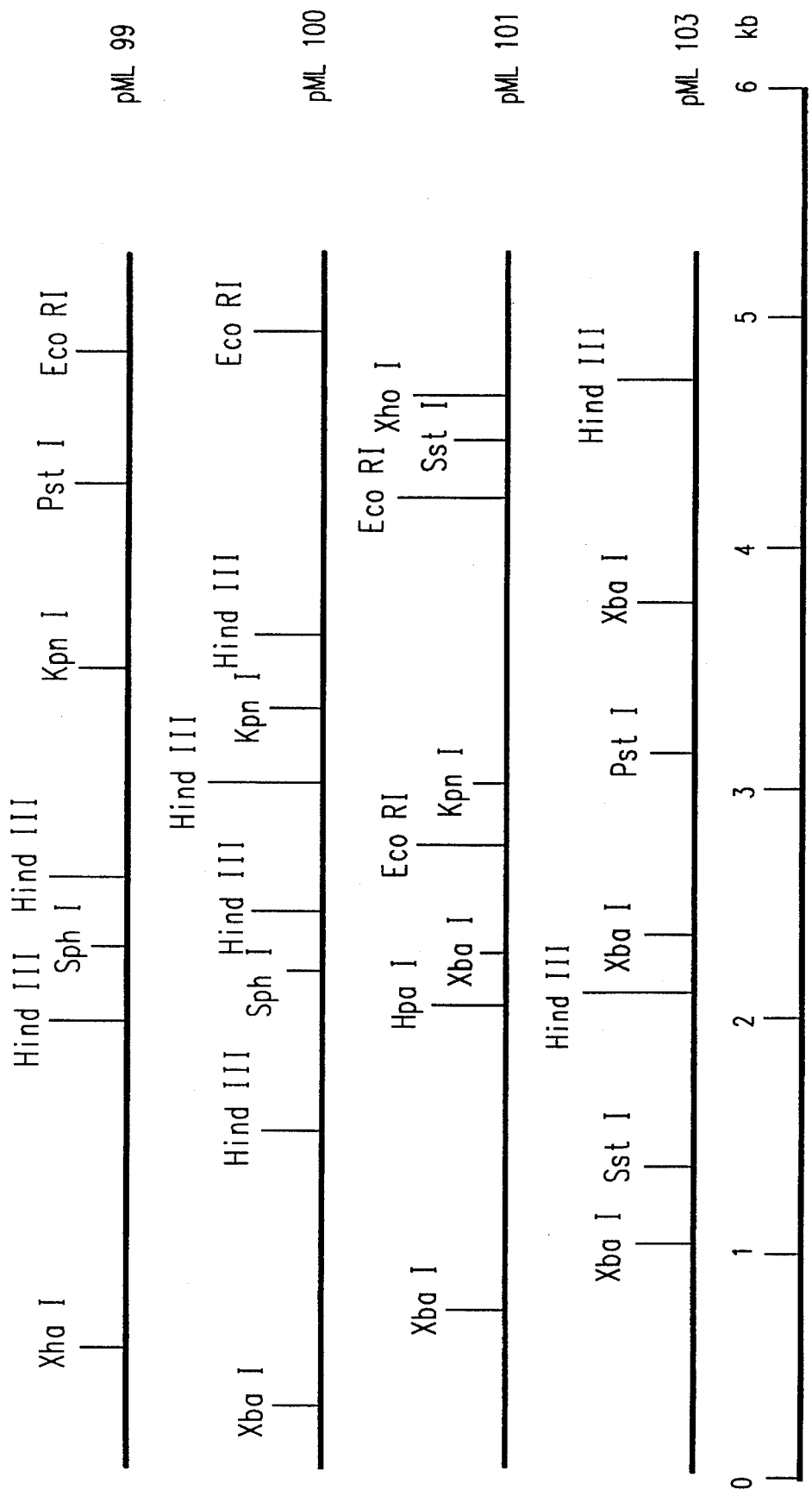
FIG. 1 shows restriction maps of four plasmid inserts recovered via selection for fenpropimorph resistance in *Saccharomyces cerevisiae* as described in Example 1. Selected restriction enzyme digestion sites are shown for each insert.

The *Saccharomyces cerevisiae* gene encoding sterol Δ14 reductase is cloned by selecting strains carrying sequences on a 2μ based vector for resistance to a morpholine fungicide. One of the plasmids so obtained is characterized and sequenced to obtain the primary structure of sterol Δ14 reductase.

By "morpholine fungicide" is meant any morpholine and structurally related piperidine compound having large ring N-substituents such as dodemorph, tridemorph, aldimorph, fenpropimorph, amorolfine, and fenpropidin which are employed as fungicides. Mixtures of morpholine fungicides may also be employed. Fenpropimorph is employed in one embodiment.

In morpholine screenings of *S. cerevisiae* strains carrying DNA sequences on a 2μ vector, plasmid inserts which produce morpholine resistance are recovered. For example, where fenpropimorph is the morpholine employed, four plasmids denoted pML99, pML100, pML101 and pML103 are recovered. Although fenpropimorph is reported to inhibit the enzymes sterol Δ14 reductase and Δ8–Δ7 isomerase, none of the inserts exhibit restriction maps resembling ERG2, the gene encoding Δ8–Δ7 isomerase. In addition, a 2μ plasmid carrying the ERG2 sequence does not produce fenpropimorph resistance.

Plasmid pML100 produces fenpropimorph resistance consistently when tested in a number of different genetic backgrounds. Tests with a panel of fungicides indicate that pML100 produces significant resistance only to the morpholine fungicides fenpropimorph, tridemorph, fenpropidin, and azasterol, compounds which have a shared site of action, the enzyme sterol Δ14 reductase. No increase in resistance is seen to a variety of other fungicides which are not sterol Δ14 reductase inhibitors, suggesting that pML100 encodes a function specific to sterol Δ14 reductase activity. Other investigators report that selection for fenpropidin or fenpropimorph resistance in other *S. cerevisiae* strains produce plasmids exhibiting properties similar to pML100 (Lorenz and Parks, cited above, and Marcireau, C., et al., cited above).

A chromosomal disruption of the sequence producing morpholine resistance results in ergosterol auxotrophy and the build-up of ignosterol, the sterol Δ14 reductase substrate. The DNA sequence which produces this activity is obtained (SEQ ID 1), which contains an open reading frame encoding an integral membrane protein, consistent with an enzyme catalyzing a reaction in the ergosterol biosynthesis pathway.

Thus, this invention provides a purified and isolated DNA sequence encoding *Saccharomyces cerevisiae* sterol Δ14 reductase. Because of the degeneracy of the genetic code, a variety of codon change combinations can be selected to form DNA that encodes sterol Δ14 reductase, so that any nucleotide deletion(s), addition(s), or point mutation(s) that result in a DNA encoding sterol Δ14 reductase are encompassed by this invention. Since certain codons are more efficient for polypeptide expression in certain types of organisms, the selection of gene alterations to yield DNA material that codes for the enzyme are preferably those that yield the most efficient expression in the type of organism which is to serve as the host of the recombinant vector. Altered codon selection may also depend upon vector construction considerations.

DNA which encodes Δ14 reductase may be natural, recombinant or synthetic. Thus, DNA of the invention may be isolated from yeast strains or constructed from oligonucleotides using conventional methods. Also encompassed are DNA sequences homologous or closely related to complementary DNA described herein, namely DNA sequences which hybridize, particularly under stringent conditions that result in pairing only between nucleic acid fragments that have a high frequency of complementary base sequences, to DNA encoding sterol Δ14 reductase particularly described herein, and RNA corresponding thereto. In addition to these sequences, DNA encompassed by this invention may contain additional sequences, depending upon vector construction sequences, that facilitate expression of the gene.

As described above, DNA encoding the sterol Δ14 reductase of this invention, or RNA corresponding thereto, are useful when introduced into a vector or plasmid, and the recombinant plasmid used to transform microbial host organisms such as *S. cerevisiae*. Other host cells such as *E. coli* may be employed in some embodiments. Especially useful in some embodiments are *S. cerevisiae* cells into which the gene has been introduced at high copy. This invention thus also provides novel, biologically functional RNA and DNA vectors and plasmids incorporating RNA and DNA sequences describing the reductase generated by standard means. Culture of host organisms stably transformed or transfected with such vectors or plasmids under conditions facilitative of large scale expression of the exogenous, vector-borne DNA or RNA sequences and isolation of the desired polypeptides from the growth medium, cellular lysates, or cellular membrane fractions are also provided.

The present invention provides for the total and/or partial manufacture of DNA sequences coding for sterol Δ14 reductase, and including such advantageous characteristics as incorporation of codons preferred for expression by selected hosts, provision of sites of cleavage by restriction by endonuclease enzymes, and provision of additional initial, terminal or intermediate DNA sequences which facilitate construction of readily expressed vectors.

DNA (and RNA) sequences of this invention code for all sequences useful in securing expression in procaryotic or eucaryotic host cells of polypeptide products having at least a part of the primary structural conformation, and one or more of the biological properties of sterol Δ14 reductase which are comprehended by: (a) the DNA sequence encoding sterol Δ14 reductase; (b) DNA sequences which hybridize to DNA sequences defined in (a) or fragments thereof; and (c) DNA sequences which, but for the degeneracy of the genetic code, would hybridize to the DNA sequences defined in (a) and (b) above. Specifically comprehended are genomic DNA sequences encoding allelic variant forms of the enzyme, and sequences encoding RNA, fragments thereof, and analogues wherein RNA or DNA sequences may incorporate codons facilitating transcription or RNA replication host cells.

Particularly useful are *S. cerevisiae* strains into which has been introduced a DNA sequence of this invention, particularly those having multiple copies of the gene. Such strains are useful in screens for sterol Δ14 reductase inhibition such as those described in copending U.S. application Ser. No. 08/107,348 filed concurrently with this application and incorporated in its entirety by reference. In an example screen, test samples are added to a yeast culture of a transformed strain such as a strain transformed with pML100, and to a corresponding control culture which does not have the introduced gene. Positive samples are identified after incubation by observation that growth inhibition in the culture having no introduced reductase gene exceeds growth in the corresponding culture having the introduced gene. In preferred embodiments, a known inhibitor of sterol Δ14 reductase is employed for comparison purposes in both cultures of the screen.

Other plasmids that produce morpholine resistance such as pML99, pML101, and pML103 described above are also useful in other screens for compounds that affect sterol biosynthesis, including screens for sterol Δ14 reductase inhibitors such as those described above. As set out more fully hereinafter, in initial genetic analyses, these plasmids show differences from pML100 in their interactions with ergosterol biosynthesis mutations. Hence, these plasmids are useful with screens such as those described above except that different yeast strains are employed. Alternatively, screening results with these plasmids can be used in combination with screening tests using pML100.

This invention also provides the polypeptide encoded by the sterol Δ14 reductase sequences of this invention, e.g., the polypeptide encoded by the open reading frame set out in SEQ ID NO 1. Correspondingly, the invention provides for manufacture (and development by site specific mutagenesis of cDNA and genomic DNA) of DNA sequences coding for microbial expression of sterol Δ14 reductase which differ from the forms specifically described herein in terms of identity or location of one or more amino acid residues (i.e., deletion and/or substitution analogues wherein one or more residues are added to a terminal or medial portion of the polypeptide), and which share the biological properties of the enzyme. In embodiments involving the microbial expression of polypeptides provided by the invention, isolation and purification employ standard methodology including, for example, preparative chromatographic separations and immunological separations, including monoclonal and/or polyclonal antibody preparations.

The sequence of pML100 exhibits partial homology to three other previously reported genes as follows (see FIG. 3): the chicken nuclear lamin B receptor (SEQ ID NO 2, Worman, H. J., et al., cited above; 101 out of 419 amino acids), the S. cerevisiae YGL022 sequence (SEQ ID NO 3, Chen, et al., cited above; 95 out of 473 amino acids), and the Schizosaccharomyces pombe stsl gene (SEQ ID NO 4, Shimanuki, M., et al., cited above; 92 out of 453 amino acids). The phenotypes of strains carrying stsl and YGL022 mutations are consistent with the hypothesis that these mutations produce lesions in erogsterol biosynthesis. The S. pombe stsl⁺gene and the S. cerevisiae YGL022 sequence have been reported to encode putative transport proteins which produce drug resistance by pumping compounds out of the cell. Mutations in these genes produce super-sensitivity to a wide variety of compounds. Drug super-sensitivity is also a phenotype associated with ergosterol biosynthesis mutations such as erg6 (Gaber, R. F., et al., Mol. Cell. Biol. 9: 3447–3456 (1989)), erg2 and erg3, presumably due to alterations in membrane function.

Physiological studies with an stsl mutant strain and a YGL022 disruption strain more particularly described hereafter and complementation studies with YGL022 provide direct proof that stsl⁺ and YGL022 encode a function in sterol biosynthesis identified as ERG4, sterol C-24(28) reductase, in S. cerevisiae. Thus, the enzymes sterol Δ14 reductase and sterol C-24(28) reductase are related enzymes, with the former catalyzing the reduction of a double bond in the D ring and the latter catalyzing the reduction of a double bond in the side chain of the sterol.

The following examples are presented to further illustrate and explain the present invention and should not be taken as limiting in any regard. Fenpropimorph, fenpropidin and tridemorph are purchased from Crescent Chemical Company, Inc., Hauppauge, N.Y. Synthetic dextrose (SD) media contains 0.7% yeast nitrogen base without amino acids, 2% dextrose and 2% agar. Yeast extract, peptone and dextrose (YEPD) media contains 1% yeast extract, 2% peptone, 2% dextrose and 2% agar.

EXAMPLE 1

This example describes the cloning and sequencing of the Saccharomyces cerevisiae gene encoding sterol Δ 14 reductase. The gene is isolated and cloned by selecting strains carrying sequences on a 2μ based vector for resistance to the morpholine fungicide, fenpropimorph, to obtain a plasmid which is shown to carry the structural gene based upon the phenotype of gene disruption strains.

Isolation and characterization of morpholine resistance plasmids. Morpholine and structurally related piperidine fungicides reportedly inhibit sterol Δ14 reductase and sterol Δ8 to Δ7 isomerase (Baloch and Mercer, cited above). The growth of S. cerevisiae strain Y294, genotype MATα, leu2-3,112, ura3-52, his3Δ, trpl, Gal⁺ (Brugge, J. S., et al., Mol. Cell. Biol. 7: 2180–2187 (1987)), in SD medium supplemented with leucine, tryptophan, uracil and histidine is inhibited by 20 µg/ml of the morpholine fungicide fenpropimorph and 50 µg/ml of the morpholine fungicide tridemorph. Fenpropimorph is used for subsequent selection experiments because of its slightly greater potency.

When Y294 cells are plated onto 20 µg/ml of fenpropimorph in SD media supplemented with leucine, tryptophan, uracil and histidine, spontaneous mutants are recovered at the rate of ~1 per $2.5 \times 10^6$ plated cells. When a library of S. cerevisiae sequences in the multicopy vector YEp13 (Nasmyth, K. A., and Tatchell, K., cell 19: 753–764 (1980)) is introduced into strain Y294 and cells are plated on SD media supplemented with tryptophan, uracil, histidine and fenpropimorph, resistant colonies appeared at the rate of ~1 per $10^{4}$, suggesting that resistance is produced by library plasmids in some of the colonies. Plasmids are cured from randomly selected resistant colonies by growing the cells in non-selective rich YEPD media and retesting for fenpropimorph resistance. In 13 strains, the plasmid-cured derivative shows sensitivity to 20 µg/ml fenpropimorph while the original plasmid carrying strain retested as fenpropimorph-resistant.

DNA is isolated from these 13 strains and plasmid DNA is recovered by E. coli transformation. Five different types of plasmid DNA are identified following an examination of restriction enzyme digestion patterns using standard methods (FIG. 1). Seven strains carry one plasmid type, pML99, which has an insert of approximately 5.5 kb. Two additional strains carry a second plasmid type, pML100, which has an insert of approximately 5.6 kb. A third plasmid type, pML101, is found in two strains and carries an insert of approximately 5.5 kb. Two additional plasmid types are each recovered from a single strain and named pML102 (~7.5 kb insert) and pML103 (~5.1 kb insert). One representative plasmid of each type is selected and subjected to extensive restriction enzyme analysis, which indicates that the insert from plasmid pML101 is contained within the insert from pML102 so that a total of four unique sequences are recovered in this selection. Restriction enzyme digestion maps of the four different insert sequences are shown in FIG. 1.

A panel of fungicides representing a variety of chemical structures and mechanisms of action listed in Table 1 is tested by disk diffusion assay against strains carrying each of these plasmids in a YEp13 vector control. All five strains show similar levels of sensitivity to all of the tested compounds with the exception of the morpholines, fenpropidin, fenpropimorph and tridemorph, and azasterol. These compounds are less active on the strains carrying the four plasmids recovered by selection for fenpropimorph resistance. Consistent with agar dilution sensitivity results, fenpropimorph is more active by disk diffusion than tridemorph. These results suggest that the cloned sequences encode functions specific to the activity of morpholines and related compounds and do not carry genes which produce general fungicide resistance, e.g., by altering cell permeability.

TABLE 1

Fungicides Used For Plasmid Characterization

| Compound | Target |
| --- | --- |
| amphotericin B | plasma membrane (polyene) |
| cerulenin | fatty acid biosynthesis |
| haloprogin | respiration |
| ketoconazole | ergosterol biosynthesis (lanosterol 14α-demethylase) |
| miconazole | ergosterol biosynthesis (lanosterol 14α-demethylase) |
| dinaconazole | ergosterol biosynthesis (lanosterol 14α-demethylase) |
| econazole | ergosterol biosynthesis (lanosterol 14α-demethylase) |
| fepropimorph | ergosterol biosynthesis (sterol Δ14 reductase/ Δ8 - Δ7 isomerase) |
| tridemorph | ergosterol biosynthesis (sterol Δ14 reductase/ Δ8 - Δ7 isomerase) |
| azasterol | ergosterol biosynthesis (sterol Δ14 reductase) |
| tolnaftate | ergosterol biosynthesis (squalene monooxygenase) |
| U18666A | ergosterol biosynthesis (squalene cyclase) |
| cycloheximide | protein biosynthesis |
| polyoxin D | chitin biosynthesis (cell wall) |
| nikkomycin | chitin biosynthesis (cell wall) |
| nocodazole | microtubule assembly |
| benomyl | microtubule assembly |
| maneb | multi-target |
| metalaxyl | rRNA biosynthesis |
| vinclozoline | lipid peroxidation |
| kanamycin | mitochondria |
| tunicamycin | glycoprotein biosynthesis |
| carboxin | succinate dehydrogenase |
| antimycin | respiration |
| 5-fluorocytosine | nucleotide metabolism |
| cyanobutarate | microtubule assembly (herbicide) |
| glyphosate | aromatic amino acid biosynthesis (herbicide) |
| phosphinothricin | glutamine biosynthesis (herbicide) |
| aminotriazole | histidine biosynthesis (herbicide) |
| sulfometuron methyl | branched chain amino acid biosynthesis (herbicide) |
| pendimethalin | microtubule assembly (herbicide) |

The library employed for the selection is prepared using DNA isolated from strain AB320 (genotype HO, ade2-1, lys2-1, trp5-2, leu2-1, canl-100, ura3-1 and/or ural-1, met4-1, Nasmyth and Tatchell, cited above). When tested, strain AB320 is found to be slightly more sensitive to fenpropimorph than strain Y294, suggesting that the cloned sequences are likely to be producing resistance as the result of gene dosage effects.

Morpholine resistance in strains transformed with multi-copy ERG2 (sterol Δ8–Δ7 isomerase) plasmids. One gene that would be expected to produce morpholine resistance at high copy is ERG2, which encodes a reported morpholine target, Δ8–Δ7 isomerase. This gene was recently cloned by the complementation of a polyene resistance mutation (Ashman, cited above). The published ERG2 restriction map is different from the restriction maps of the four sequences recovered by morpholine resistance selection. Since it is possible that the ERG2 sequence is missed in the morpholine resistance screen, this gene is introduced into S. cerevisiae strain Y294 on the 2μ based plasmid, pML104, constructed by subcloning the ERG2 gene on a 2.1 kb HindIII fragment from plasmid PIU406 (Ashman, et al., cited above) into the HindIII site of plasmid YEp351. This strain shows no increase in fenpropimorph resistance relative to YEp351-transformed control strain. Plasmid pML104 does, however, produce nystatin sensitivity when introduced into the erg2 mutant strain WAO (Ashman, et al., cited above), demonstrating that plasmid pML104 carries a functional ERG2 gene. Sterol Δ8–Δ7 isomerase may not over-express when present on a 2μ based, multi-copy plasmid, or the enzyme may not be a morpholine target in S. cerevisiae.

Characterization of fenpropimorph resistance plasmid pML100. The four fenpropimorph-resistance plasmids pML99, pML100, pML101, and pML103 are transformed into three ergosterol pathway mutant strains, erg2 (denoted WAO, genotype MATa, his7-2, leu2-3,112, ura3-52, erg2-3, Ashman, et al., cited above); erg3 (denoted XML39-1d, geno-type MATa, leu2-3,112, erg3-2); and erg6 (denoted XML40-1c, genotype MATa, leu2-3,112, gal2, erg6-5). Morpholine sensitivity is determined by disk diffusion assay on appropriately supplemented SD medium using tridemorph and fenpropimorph. A zone size difference of greater than 3 mm performed in duplicate is recorded as resistance. The ergosterol pathway mutant strains vary in absolute level of morpholine sensitivity, and all resistance and sensitivity determinations are reported relative to vector (YEp13)-transformed control strains. The results are tabulated in Table 2. Only plasmid pML100 transformants are consistently fenpropimorph-resistant in all genetic backgrounds.

TABLE 2

Plasmid Phenotype in Ergosterol Pathway Mutant Strains

| Strain | Ergosterol Genotype | Plasmid | Morpholine Resistance |
| --- | --- | --- | --- |
| Y294 | ERG+ | YEp13 | – |
| Y294 | ERG+ | pML99 | + |
| Y294 | ERG+ | pML100 | + |
| Y294 | ERG+ | pML101 | + |
| Y294 | ERG+ | pML103 | + |
| WAO | erg2 | YEp13 | – |
| WAO | erg2 | pML99 | – |
| WAO | erg2 | pML100 | + |
| WAO | erg2 | pML101 | – |
| WAO | erg2 | pML103 | – |
| XML39-1d | erg3 | YEp13 | – |
| XML39-1d | erg3 | pML99 | + |
| XML39-1d | erg3 | pML100 | + |
| XML39-1d | erg3 | pML101 | – |
| XML39-1d | erg3 | pML103 | +/–* |
| XML40-1c | erg6 | YEp13 | – |
| XML40-1c | erg6 | pML99 | + |
| XML40-1c | erg6 | pML100 | + |
| XML40-1c | erg6 | pML101 | – |
| XML40-1c | erg6 | pML103 | +/–* |

*–Resistance was observed with fenpropimorph but not tridemorph.

Resistance is also seen with other morpholine anti-fungals (tridemorph and fenpropidin) and azasterol, all of which are reported to be inhibitors of sterol Δ14 reductase. However, no increase is seen to a variety of other fungicides which are not sterol Δ14 reductase inhibitors. Since resistance occurs only to sterol Δ14 reductase inhibitors and is seen for such inhibitors from two different chemical classes, it is likely that pML100 encodes a function specific to sterol Δ14 reductase activity.

Figure 2:
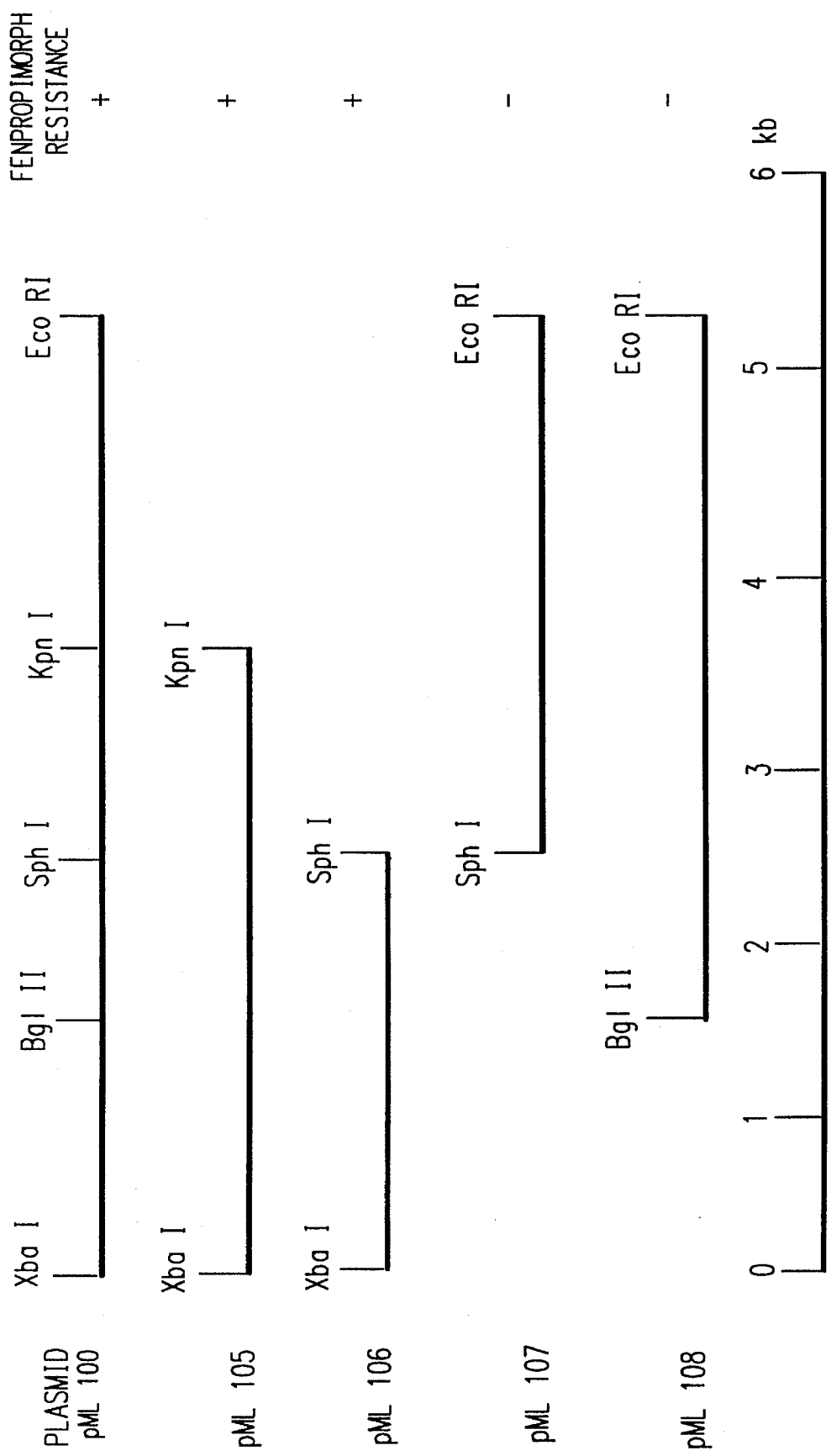
FIG. 2 shows fenpropimorph resistance of subclones of pML100, a plasmid containing the cloned sterol Δ14 reductase gene.

Subclones of the pML100 insert are prepared in the yeast shuttle vector YEp352, transformed into yeast strain Y294, and tested for fenpropimorph resistance. As shown in FIG. 2, the fenpropimorph resistance region is limited to a 2.5 kb SphI/XbaI fragment located near one side of the insert/vector border.

Plasmid pML106, which contains this fragment in vector YEp352, is cleaved with BglII, which cuts once at a site near the middle of the SphI/XbaI fragment. A 3.0 kb BglII fragment containing the S. cerevisiae LEU2 gene is isolated from plasmid YEp13 and ligated into this BglII cite, producing plasmid pML108. The disrupted 5.5 kb SphI/XbaI fragment containing the LEU2 gene is isolated from plasmid pML108 and used to transform S. cerevisiae strain YPH501 to leucine prototrophy. Transformants in which the 5.5 kb SphI/XbaI fragment replaced the 2.5 kb SphI/XbaI fragment in one chromosomal homologue are identified by Southern analysis.

Tetrads from one such transformant (strain YPH501-2-1) are dissected and the spores germinated under anaerobic conditions on YEPD medium supplemented with Tween® 80 (500 μg/ml) and ergosterol (20 μg/ml). Strain YPH501-2-1 shows low (approximately 50%) spore viability, and no tetrads are recovered. This is found to be a property of strain YPH501 which showed a similar low level of spore viability when spores from the host strain are germinated anaerobically. By random spore analysis, 15 of 32 segregants are both Leu⁺ and obligate anaerobes, suggesting that the disruption has produced a genetic lesion in sterol biosynthesis. (The remaining 17 segregants are Leu⁻ and grow aerobically.)

One such obligate anaerobe segregant, denoted YPH501-2-1-3C, is analyzed for sterol content. The strain is grown anaerobically on YEPD medium containing ergosterol (5 μg/ml) to facilitate sterol uptake. After one day, the cells are harvested, washed in saline, resuspended in YEPD medium with no added sterol and grown for an additional 2 days to deplete cellular sterol. After 3 days, sterols are extracted from stationary phase yeast cells into n-heptane and analyzed by ultraviolet (UV) between 200 and 300 nm, gas chromatography (GC) and gas chromatographymass spectrometry (GC-MS). GC-MC analyses are performed on a Hewlett Packard (HP) 5980 instrument using a 30 meter× 0.25 mm HP-5 column with a 25 micron film thickness. The column temperature is programmed from 280° C. to 300° C. with the initial temperature maintained for 2 minutes and increased at 3° C./minute. The final temperature is held for 6 minutes. The mass spectrometer is operated in the electron impact ionization mode at 70 eV. High pressure liquid chromatography (HPLC) analyses are performed using a reverse phase column (2.1×100 mm) packed with 5 micron spherical C18 bonded silica. Sterol samples are dissolved in a methanol:ethyl acetate (1:1) mixture and eluted from HPLC with 95% acetonitrile in water at 1 ml/minute. The detection wavelength is 270 nm.

UV analysis demonstrates a 250 nm broad peak indicative of a sterol containing a conjugated double bond system involving C-8(9) and C-14(15). GC analyses indicate a major peak with the relative retention time of 1.30 consistent with ignosterol (ergosta-8,14-dien-3β-ol, molecular weight 398), the sterol Δ14 reductase substrate. GC-MS analysis confirms that the major sterol accumulating in this disrupted strain is ignosterol. Small amounts of lanosterol, approximately 5%, are also observed, consistent with a block in the sterol pathway downstream of lanosterol and affecting the reduction of the C-14 double bond. The accumulation of ignosterol indicates a genetic lesion in sterol Δ14 reductase activity.

DNA sequence analysis of plasmid pML100. DNA sequences are performed using an Applied Biosystems automatic DNA sequencer from Applied Biosystems, Inc., Foster City, Calif. 94404, following the manufacturer's directions. Dye primers and dye terminators are used as appropriate for the insert to be sequenced. Oligonucleotides used for sequencing with dye terminators are synthesized using an Applied Biosystems oligonucleotide synthesizer according to the manufacturer's directions.

The DNA sequence of the 2.5 kb SphI/XbaI fragment of plasmid pML100 is set out in the Sequence Listing section hereinafter as SEQ ID NO 1. An open reading frame of 1314 base pairs is identified starting at an ATG codon at position 419 within the sequence. No other open reading frame of significant size is present within this fragment. Upstream of this ATG codon is an AT-rich sequence (66%), typical of many functionally expressed S. cerevisiae genes. This open reading frame encodes a 438 amino acid, 50.5 kilo-dalton basic (pI=9.2), presumptive integral membrane protein which, based upon hydropathy analysis using a computer program that progressively evaluates the hydrophilicity and hydrophobicity of a protein along its amino acid sequence (Kyte, J., and Doolittle, R. F., J. Mol. Biol. 157: 105–132 (1982)), contains 8 or 9 putative transmembrane domains.

EXAMPLE 2

The open reading frame of the plasmid pML100 DNA sequence of Example 1 is compared to other sequences in this example.

Figure 3B:
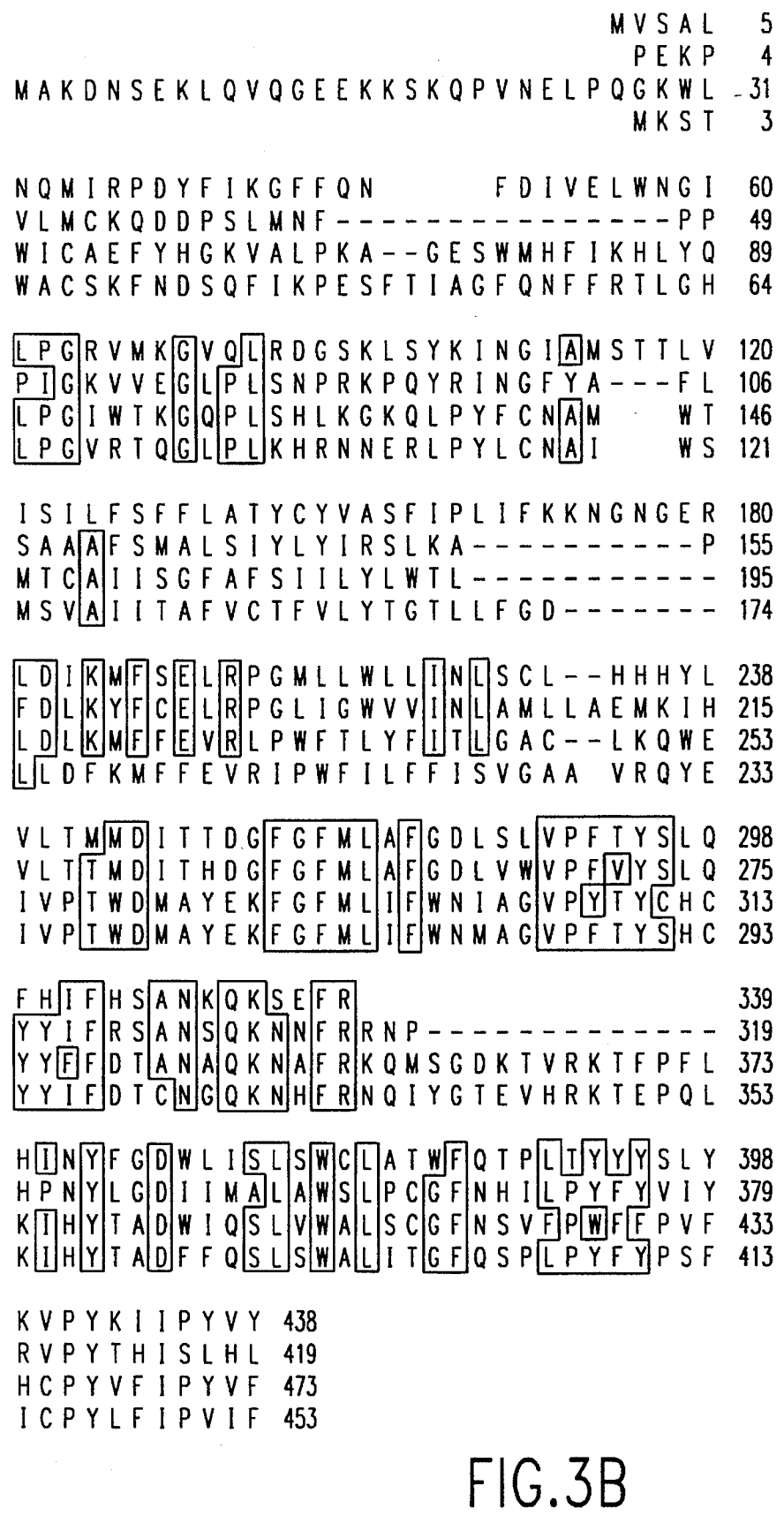

The sequence is compared with sequences deposited in the Genbank® DNA sequence data base. Three sequences show partial homology: the chicken nuclear lamin B receptor (SEQ ID NO 2, Worman, H. J., et al., cited above; 101 out of 419 amino acids), the S. cerevisiae YGL022 sequence (SEQ ID NO 3, Chen, et al., cited above; 95 out of 473 amino acids) and the S. pombe stsl gene (SEQ ID NO 4, Shimanuki, M., et al., cited above; 92 out of 453 amino acids). A comparison of the amino acid sequences of the three yeast genes is shown in FIG. 3. A certain amount of sequence similarity is seen along the entire length of the three sequences and is particularly pronounced at the carboxy termini of these polypeptides.

EXAMPLE 3

The physiological characteristics of mutant phenotypes Schizosaccharomyces pombe stsl and Saccharomyces cerevisiae YGL022 found to be somewhat homologous to the pML100 sequence as described in Example 2 are characterized in this example.

S. pombe strains HM123 and JY6(stsl⁺) and 111-1A (stsl) are obtained and analyzed for their sterol profiles. UV, GC-MC and HPLC analyses are carried out as described in Example 1 above; proton nuclear magnetic resonance (NMR) analysis on samples dissolved in d₆-acetone is obtained on a Brunker AMX300 MHz spectrometer, Brunker Instruments, Inc., Billerica, Mass. 01821. As set out in the data summarized in Table 3 below, while the wild-type strains accumulate ergosterol and small amounts of lanosterol and perhaps 24-methylene-dihydrolanosterol (molecular weight 440), the mutant strain acccumulated principally the tetraene, ergosta-5,7,22,24(28)-tetraen-3-β-ol.

The conversion of the tetraene to ergosterol is considered to be the last step in ergosterol biosynthesis and the gene encoding this enzymatic step has been designated ERG4 in *S. cerevisiae* as discussed above. Whereas ergosterol gives absorption maxima at 262, 271, 282 and 293 nm, the precursor 24(28)-ergosterol gives absorption maxima at 232 nm reflecting the presence of a conjugated double bond system in the sterol side chain. The identity of the tetraene is confirmed by GC-MS and NMR.

GC-MS analysis shows a molecular ion at M/Z 394, 2 atomic mass units less than ergosterol. An ion is present at M/Z 123 which has no counterpart in the spectrum of ergosterol. This ion is proposed to represent the side chain fragment $C_9H_{15}$ indicating the presence of two unsaturations. Consistent with the UV and GC-MS analyses, the structure of the conjugated side chain is substantiated by proton NMR signals indicative of the exomethylene protons (chemical shift 4.71 and 4.73, broad singlets) and signals for H22 (chemical shift 5.52, $J_{21,22}=8.8$ Hz, $J_{22,23}=15.8$ Hz) and H23 (chemical shift 5.87, $J_{23,22}=15.8$ Hz). The chemical shift values for the latter two protons are considerably downfield from their position in ergosterol, which has a chemical shift of about 5.25, reflecting the deshielding effects of the conjugation with the C-24(28) double bond. This provides further evidence that an additional double bond is present in the sterol side chain.

Upon transformation of strain TP111-1A with a plasmid pST2SC which contains the wild-type C-24(28) reductase gene, an ergosterol profile is observed. However, when selection pressure is removed such that the plasmid is lost, the tetraene profile is restored, indicating that ergosterol synthesis requires the presence of the plasmid containing the wild-type gene (Table 3). Thus, stsl⁺ appears to encode a protein in the ergosterol biosynthesis pathway.

YGL022 is then characterized. A leaky, *S. cerevisiae* erg4 mutant strain (Molzahn, S. W., and Woods, R. A., *J. Gen Microbiol.* 72: 339–348 (1972)) is subjected to sterol analysis as described above. Approximately 35% ergosterol and 60% ergosta-5,7,22,24(28)-tetraen-3β-ol accumulates. When this strain is transformed with plasmid pA-B6.5 carrying the YGL022 sequence (Balzi, E., et al., *J. Biol. Chem.* 262: 16871–16879 (1987)) and retested, mostly ergosterol is detected (Table 3).

To confirm these findings, the open reading frame in YGL022 (in plasmid pA-B6.5) is disrupted by deleting an approximately 0.6 kb SmaI/AccI fragment internal to the open reading frame and replacing this with an approximately 2.2 kb HpaI fragment carrying the LEU2 gene (in a gene disruption construction similar to that described by Chen, et al., cited above). This sequence is released from the plasmid by XhoI and BamHI digestion, and the linear sequence is transformed into a diploid strain XML25 which is then sporulated. Integration of the construction into the YGL022 sequence is confirmed by Southern analysis.

Forty-seven tetrads are studied and all show 2:2 segration for leucine prototrophy. Leucine auxotrophic segregants are all wild-type for drug sensitivity while leucine prototrophic segregants show increased sensitivity to cycloheximide. One tetrad is analyzed for ergosterol content. The leucine auxotrophic segregants synthesize ergosterol while the leucine prototrophic segretants do not synthesize ergosterol and accumulate ergosta-5,7,22,-4(28)-tetraen-3β-ol (Table 3). This indicates that the YGL022 sequence is required for sterol C-24(28) reductase activity (ERG4) in *S. cerevisiae*.

TABLE 3

Sterol Accumulation Patterns in Wild-Type and erg4 Yeast Strains

| Species | Strain | Genotype | % Sterol Content Ergosterol | 24(28) Tetraene | Other Sterol |
|---|---|---|---|---|---|
| S. pombe | HM123 | erg4+ | 86 | 0 | 14 |
| S. pombe | JY-6 | erg4+ | 94 | 0 | 6 |
| S. pombe | TP111-1A | erg4 | 0 | 94 | 6 |
| S. pombe | TP111-1A (pST2Sc) | erg4+ | 100 | 0 | 0 |
| S. pombe | TP111-1A cured | erg4 | 0 | 100 | 0 |
| S. cerevisiae | erg4-1A | erg4+/− | 29 | 68 | 3 |
| S. cerevisiae | erg4-1A (pA-B6.5) | ERG4 | 83 | 5 | 12 |
| S. cerevisiae | erg4-1A cured | erg+/− | 37 | 57 | 6 |
| S. cerevisiae | XML25-2-1A | erg4Δ | 0 | 97 | 3 |
| S. cerevisiae | XML25-2-1B | ERG4 | 91 | 0 | 9 |
| S. cerevisiae | XML25-2-1C | erg4Δ | 0 | 98 | 2 |
| S. cerevisiae | XML25-2-1D | ERG4 | 88 | 0 | 12 |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

BIBLIOGRAPHY

Ashman, W. H., et al., *Lipids* 26: 628–632 (1991).
Baloch, R. and Mercer, I., *Phytochemistry* 26: 663–668 (1987v).
Balzi, E., et al., *J. Biol. Chem.* 262: 16871–16879 (1987).
Brugge, J. S., et al., *Mol. Cell. Biol.* 7: 2180–2187 (1987).
Chen, W., et al., *Yeast* 7: 305–308 (1991).
Gaber, R. F., et al., *Mol. Cell. Biol.* 9: 3447–3456 (1989).
Kyte, J., and Doolittle, R. F., *J. Mol. Biol.* 157: 105–132 (1982).
Lorenz, T., and Parks, L. W., *DNA and Cell Biol.* 11: 685–692 (1992).
Marcireau, C., et al., *Curr. Genet.* 22: 267–272 (1992).
Molzahn, S. W., and Woods, R. A., *J. Gen Microbiol.* 72: 339–348 (1972).
Nasmyth, K. A., and Tatchell, K., *Cell* 19: 753–764 (1980).
Paltauf, F., et al., in Jones, E. W., et al., eds., *The Molecular and Cellular Biology of the Yeast Saccharomyces, Gene Expression,* Cold Spring Harbor Laboratory Press, 1992, pages 415, 418–420, 424–428, and 434–437.
Shimanuki, M., et al., *Mol. Biol. Cell* 3:263–273 (1992).
Worman, H. J., et al., *J. Cell Biology* 111: 1535–1542 (1990).

We claim:

1. A *Saccharomyces cerevisiae* sterol Δ14 reductase encoded by a DNA sequence which hybridizes under stringent conditions with the nucleotides numbered 419 to 1732 of SEQ ID NO: 1.

2. A *S. cerevisiae* sterol Δ14 reductase according to claim 1 having an amino acid sequence depicted in residues numbered 1 to 438 of SEQ ID NO: 5.

3. A composition comprising isolated and purified *S. cerevisiae* sterol Δ14 reductase.

4. A composition according to claim 3 wherein the reductase has the amino acid sequence depicted in residues numbered 1 to 438 of SEQ ID NO: 5.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 2528 bases and 438 amino acids
        ( B ) TYPE: nucleic acid and amino acid
        ( C ) STRANDEDNESS: double
        ( D ) TOPOLOGY: linear ( i i ) MOLECULE TYPE:
        ( A ) DESCRIPTION: DNA encoding a polypeptide ( v ) FRAGMENT TYPE: entire sequence ( v i ) IMMEDIATE SOURCE: *Saccharomyces cerevisiae*
        clone ( i x ) FEATURE:
        ( D ) OTHER INFORMATION: sterol Δ14 reductase gene,
        translated
        polypeptide and flanking DNA ( x i ) SEQUENCE DESCRIPTION: SEQ ID NO: 1:

```
ATATATATAT  ACCTCTTGCC  AGCAACAGGC  CAGTTATAAG  TTAAAATTAA                50

TATGTGACGC  ACTTCTGAAA  CAGTATTGAA  ACAGTATTGA  AACATATGTA               100

TTACCCGGAC  TCTGCATGCT  CTGTCGTTCA  TTTTATTTTC  ACCTAAACGA               150

AAATCCCGTG  AAAAAAATTT  ATATCGCCTT  TCGCTCTTTT  GTATGTAGGC               200

ATCATCGGAA  ATTTGCATTG  TGTGAAGGTT  GTGCATATAA  AGGGTTTTGC               250

ATAACGGACG  TTTTTCACGT  ACTCCGTCTG  AGCATCAAGT  GAGGCTTGAG               300

TTTACGTTTG  TTTTTAATAA  TCAGTTTTCA  TTCTACTATT  TTCTTGCGCA               350

ATTGCTTATC  AGATAGACCT  TGTAAACAGC  ATAGGAGTAA  AGACAAATTC               400

GGTGTAGAGA  ATAAAAGG  ATG  GTA  TCA  GCT  TTG  AAT  CCC  AGA  ACT  ACA  GAG    451
                    Met  Val  Ser  Ala  Leu  Asn  Pro  Arg  Thr  Thr  Glu
                                        5                              10

TTT  GAA  TTT  GGT  GGG  CTG  ATT  GGT  GCC  TTA  GGC  ATC  AGC  ATA  GGG     496
Phe  Glu  Phe  Gly  Gly  Leu  Ile  Gly  Ala  Leu  Gly  Ile  Ser  Ile  Gly
               15                      20                      25

CTG  CCT  GTT  TTC  ACT  ATC  ATC  TTG  AAT  CAA  ATG  ATA  AGG  CCC  GAT     541
Leu  Pro  Val  Phe  Thr  Ile  Ile  Leu  Asn  Gln  Met  Ile  Arg  Pro  Asp
               30                      35                      40

TAT  TTT  ATT  AAG  GGA  TTT  TTC  CAG  AAT  TTC  GAT  ATA  GTT  GAG  CTT     586
Tyr  Phe  Ile  Lys  Gly  Phe  Phe  Gln  Asn  Phe  Asp  Ile  Val  Glu  Leu
               45                      50                      55

TGG  AAC  GGT  ATC  AAG  CCA  TTG  CGC  TAC  TAT  CTG  GGC  AAT  CGT  GAA     631
Trp  Asn  Gly  Ile  Lys  Pro  Leu  Arg  Tyr  Tyr  Leu  Gly  Asn  Arg  Glu
               60                      65                      70

TTA  TGG  ACT  GTC  TAT  TGC  CTG  TGG  TAT  GGA  ATA  CTG  GCA  GTT  TTG     676
Leu  Trp  Thr  Val  Tyr  Cys  Leu  Trp  Tyr  Gly  Ile  Leu  Ala  Val  Leu
               75                      80                      85

GAC  GTC  ATT  TTA  CCG  GGC  AGA  GTC  ATG  AAG  GGT  GTT  CAG  TTA  AGG     721
Asp  Val  Ile  Leu  Pro  Gly  Arg  Val  Met  Lys  Gly  Val  Gln  Leu  Arg
               90                      95                     100

GAT  GGT  TCG  AAG  CTT  TCG  TAT  AAG  ATC  AAT  GGA  ATT  GCC  ATG  TCT     766
Asp  Gly  Ser  Lys  Leu  Ser  Tyr  Lys  Ile  Asn  Gly  Ile  Ala  Met  Ser
              105                     110                     115

ACA  ACT  TTG  GTC  TTA  GTT  TTG  GCT  ATC  AGA  TGG  AAA  TTG  ACT  GAT     811
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Thr | Thr | Leu | Val | Leu | Val | Leu | Ala | Ile | Arg | Trp | Lys | Leu | Thr | Asp |      |
|     |     |     | 120 |     |     |     |     | 125 |     |     |     |     | 130 |     |      |
| GGA | CAA | TTG | CCT | GAA | TTG | CAA | TAT | CTG | TAT | GAA | AAT | CAC | GTT | AGT | 856  |
| Gly | Gln | Leu | Pro | Glu | Leu | Gln | Tyr | Leu | Tyr | Glu | Asn | His | Val | Ser |      |
|     |     |     | 135 |     |     |     |     | 140 |     |     |     |     | 145 |     |      |
| TTA | TGC | ATA | ATA | TCT | ATT | TTG | TTT | TCG | TTC | TTT | TTG | GCG | ACG | TAC | 901  |
| Leu | Cys | Ile | Ile | Ser | Ile | Leu | Phe | Ser | Phe | Phe | Leu | Ala | Thr | Tyr |      |
|     |     |     | 150 |     |     |     |     | 155 |     |     |     |     | 160 |     |      |
| TGC | TAT | GTT | GCC | AGC | TTC | ATA | CCA | TTG | ATC | TTC | AAG | AAA | AAT | GGT | 946  |
| Cys | Tyr | Val | Ala | Ser | Phe | Ile | Pro | Leu | Ile | Phe | Lys | Lys | Asn | Gly |      |
|     |     |     | 165 |     |     |     |     | 170 |     |     |     |     | 175 |     |      |
| AAT | GGC | AAA | AGG | GAA | AAG | ATC | TTA | GCA | CTA | GGT | GGA | AAT | TCA | GGA | 991  |
| Asn | Gly | Lys | Arg | Glu | Lys | Ile | Leu | Ala | Leu | Gly | Gly | Asn | Ser | Gly |      |
|     |     |     | 180 |     |     |     |     | 185 |     |     |     |     | 190 |     |      |
| AAC | ATC | ATT | TAC | GAT | TGG | TTT | ATT | GGT | AGA | GAA | CTG | AAC | CCT | CGT | 1036 |
| Asn | Ile | Ile | Tyr | Asp | Trp | Phe | Ile | Gly | Arg | Glu | Leu | Asn | Pro | Arg |      |
|     |     |     | 195 |     |     |     |     | 200 |     |     |     |     | 205 |     |      |
| CTC | GGC | CCA | TTA | GAT | ATC | AAG | ATG | TTT | TCA | GAG | TTG | AGA | CCC | GGC | 1081 |
| Leu | Gly | Pro | Leu | Asp | Ile | Lys | Met | Phe | Ser | Glu | Leu | Arg | Pro | Gly |      |
|     |     |     | 210 |     |     |     |     | 215 |     |     |     |     | 220 |     |      |
| ATG | TTG | TTA | TGG | TTA | CTG | ATC | AAT | CTT | TCC | TGT | CTG | CAT | CAC | CAT | 1126 |
| Met | Leu | Leu | Trp | Leu | Leu | Ile | Asn | Leu | Ser | Cys | Leu | His | His | His |      |
|     |     |     | 225 |     |     |     |     | 230 |     |     |     |     | 235 |     |      |
| TAC | CTG | AAG | ACT | GGT | AAA | ATC | AAC | GAT | GCA | TTG | GTC | TTG | GTT | AAT | 1171 |
| Tyr | Leu | Lys | Thr | Gly | Lys | Ile | Asn | Asp | Ala | Leu | Val | Leu | Val | Asn |      |
|     |     |     | 240 |     |     |     |     | 245 |     |     |     |     | 250 |     |      |
| TTC | TCG | CAA | GGA | TTT | TAC | ATT | TTC | GAT | GGA | GTA | CTA | AAC | GAG | GAA | 1216 |
| Phe | Ser | Gln | Gly | Phe | Tyr | Ile | Phe | Asp | Gly | Val | Leu | Asn | Glu | Glu |      |
|     |     |     | 255 |     |     |     |     | 260 |     |     |     |     | 265 |     |      |
| GGT | GTA | TTA | ACC | ATG | ATG | GAT | ATC | ACT | ACA | GAT | GGG | TTT | GGT | TTC | 1261 |
| Gly | Val | Leu | Thr | Met | Met | Asp | Ile | Thr | Thr | Asp | Gly | Phe | Gly | Phe |      |
|     |     |     | 270 |     |     |     |     | 275 |     |     |     |     | 280 |     |      |
| ATG | CTA | GCG | TTT | GGT | GAC | TTA | AGT | TTA | GTT | CCA | TTC | ACC | TAC | TCA | 1306 |
| Met | Leu | Ala | Phe | Gly | Asp | Leu | Ser | Leu | Val | Pro | Phe | Thr | Tyr | Ser |      |
|     |     |     | 285 |     |     |     |     | 290 |     |     |     |     | 295 |     |      |
| TTA | CAA | GCG | CGT | TAC | TTG | AGT | GTT | TCC | CCT | GTG | GAA | TTG | GGA | TGG | 1351 |
| Leu | Gln | Ala | Arg | Tyr | Leu | Ser | Val | Ser | Pro | Val | Glu | Leu | Gly | Trp |      |
|     |     |     | 300 |     |     |     |     | 305 |     |     |     |     | 310 |     |      |
| GTG | AAA | GTT | GTC | GGT | ATA | TTA | GCC | ATA | ATG | TTT | TTG | GGT | TTC | CAC | 1396 |
| Val | Lys | Val | Val | Gly | Ile | Leu | Ala | Ile | Met | Phe | Leu | Gly | Phe | His |      |
|     |     |     | 315 |     |     |     |     | 320 |     |     |     |     | 325 |     |      |
| ATC | TTC | CAC | TCG | GCA | AAT | AAG | CAA | AAA | TCT | GAG | TTT | AGA | CAA | GGT | 1441 |
| Ile | Phe | His | Ser | Ala | Asn | Lys | Gln | Lys | Ser | Glu | Phe | Arg | Gln | Gly |      |
|     |     |     | 330 |     |     |     |     | 335 |     |     |     |     | 340 |     |      |
| AAA | TTA | GAA | AAT | CTA | AAA | AGT | ATT | CAG | ACA | AAG | CGT | GGT | ACA | AAG | 1486 |
| Lys | Leu | Glu | Asn | Leu | Lys | Ser | Ile | Gln | Thr | Lys | Arg | Gly | Thr | Lys |      |
|     |     |     | 345 |     |     |     |     | 350 |     |     |     |     | 355 |     |      |
| TTA | TTA | TGT | GAC | GGG | TGG | TGG | GCT | AAA | TCA | CAG | CAT | ATC | AAT | TAC | 1531 |
| Leu | Leu | Cys | Asp | Gly | Trp | Trp | Ala | Lys | Ser | Gln | His | Ile | Asn | Tyr |      |
|     |     |     | 360 |     |     |     |     | 365 |     |     |     |     | 370 |     |      |
| TTT | GGC | GAT | TGG | CTG | ATT | TCA | TTA | AGT | TGG | TGT | TTG | GCC | ACC | TGG | 1576 |
| Phe | Gly | Asp | Trp | Leu | Ile | Ser | Leu | Ser | Trp | Cys | Leu | Ala | Thr | Trp |      |
|     |     |     | 375 |     |     |     |     | 380 |     |     |     |     | 385 |     |      |
| TTC | CAA | ACT | CCC | TTG | ACA | TAT | TAC | TAC | TCG | TTG | TAC | TTC | GCC | ACG | 1621 |
| Phe | Gln | Thr | Pro | Leu | Thr | Tyr | Tyr | Tyr | Ser | Leu | Tyr | Phe | Ala | Thr |      |
|     |     |     | 390 |     |     |     |     | 395 |     |     |     |     | 400 |     |      |
| TTG | TTA | TTA | CAC | CGT | CAA | CAA | CGT | GAT | GAG | CAC | AAG | TGC | CGC | CTG | 1666 |
| Leu | Leu | Leu | His | Arg | Gln | Gln | Arg | Asp | Glu | His | Lys | Cys | Arg | Leu |      |
|     |     |     | 405 |     |     |     |     | 410 |     |     |     |     | 415 |     |      |
| AAA | TAT | GGC | GAA | AAT | TGG | GAA | GAA | TAC | GAA | AGA | AAA | GTT | CCT | TAC | 1711 |

| | | | | | | | | | | | | | | |
|---|---|---|---|---|---|---|---|---|---|---|---|---|---|---|
| Lys | Tyr | Gly | Glu | Asn | Trp | Glu | Glu | Tyr | Glu | Arg | Lys | Val | Pro | Tyr |
| | | | 420 | | | | 425 | | | | | | 430 | |

| | | | | | | |
|---|---|---|---|---|---|---|
| AAG | ATC | ATT | CCA | TAT | GTT | TAT TAAGTTTTC TACCACTGCT ATTTTCTTCA | 1762 |
| Lys | Ile | Ile | Pro | Tyr | Val | Tyr |
| | | | 435 | | | |

| | | | | |
|---|---|---|---|---|
| TTATCTATGT | ATGTGTGTAT | ACATGTTATG | TATTGGGTGA | GTATGAGGAA | 1812 |
| GAAGAAGAAT | AACAATTGAA | AACGCTGGAA | AAATTAAAAG | GGGTGGCGGT | 1862 |
| CTATCTATGC | AACGCTCCCC | TTTTCGTTAC | ATGAACACAT | CAAACTTGTA | 1912 |
| TATCCTTTGA | GTGTTCTTTA | ATCAAGTCAT | CTTGGTATTT | TAGTAGCGTT | 1962 |
| TCCACTACTT | TAGGGACAAA | TTCAGACCTA | ACCAATCCAT | CAAAAGCATC | 2012 |
| AAACCCTTGC | GACAAAATCG | GAATATCAGA | CTCGCCATGC | ATAAACTCTG | 2062 |
| GAATTTCTAG | TTTCCCGTCC | GCAAGTATGC | CGTCATCATC | CTCGTCGTCC | 2112 |
| TTATTAGTAT | CCAAATTTGT | CACTTTGACG | TTCATCGACA | ACTGTAAGTC | 2162 |
| AAAGTAGCAA | ATCGCCTTGC | CCTTCCTTTG | AGATACGTTG | GAGTCACCGG | 2212 |
| TGATGCTACT | CACCTGGGTT | AACTCAATTT | TGCTCTTCCC | ATCAGAGGAA | 2262 |
| ACAGTGGACA | AACTCGTTAA | TTTACCGTTC | AAGTAGTCCT | TAGACCAAGG | 2312 |
| TAAGGTGTTT | TTATCCACCC | AATGCCAGTT | ATTTGGATTC | AAGACAACCA | 2362 |
| TATTTTATCG | TAAATGTGTT | GTAACTTCC | GATCGTTTCA | AACTTTAGTA | 2412 |
| GTAGTTTGAT | GATTTTGTCC | AAAAAGTATT | TGCTTAAATT | TCAGCTTTTT | 2462 |
| TCTTCTTCAT | ATGTATTTCT | TTTTTTCCTC | GCTTTCTCTG | CCCACTTTTT | 2512 |
| TCTTCTGTCT | TCTAGA | | | | 2528 |

( 2 ) INFORMATION FOR SEQ ID NO:2:

( i ) SEQUENCE CHARACTERISTICS:
        ( A ) LENGTH: 419 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( i x ) FEATURE:
        ( A ) NAME/KEY: chicken
            nuclear lamin B receptor ( x ) PUBLICATION INFORMATION:
        ( A ) AUTHORS: H.J. Worman, C.D. Evans, and G.
            Blobel
        ( B ) TITLE: (excerpt): The Lamin B Receptor of the
            Nuclear Envelope Inner Membrane
        ( C ) JOURNAL: *Journal of Cell Biology*
        ( D ) VOLUME: 111
        ( F ) PAGES: 1535-1542
            Sequence set out in Figure 5, page 1539
        ( G ) DATE: 1990
        ( K ) RELEVANT RESIDUES IN SEQ ID NO: 190 to 608

( x i ) SEQUENCE DESCRIPTION: SEQ ID NO: 2:

| | | | | | | | | | | | | | | |
|---|---|---|---|---|---|---|---|---|---|---|---|---|---|---|
| Pro | Glu | Lys | Pro | Ser | Ser | Lys | Thr | Lys | Glu | Leu | Glu | Phe | Gly | Gly |
| | | | | 5 | | | | 10 | | | | | | 15 |
| Arg | Phe | Gly | Thr | Phe | Met | Leu | Met | Phe | Phe | Leu | Pro | Ala | Thr | Val |
| | | | | 20 | | | | 25 | | | | | | 30 |
| Leu | Tyr | Leu | Val | Leu | Met | Cys | Lys | Gln | Asp | Asp | Pro | Ser | Leu | Met |
| | | | | 35 | | | | 40 | | | | | | 45 |
| Asn | Phe | Pro | Pro | Leu | Pro | Ala | Leu | Glu | Ser | Leu | Trp | Glu | Thr | Lys |
| | | | | 50 | | | | 55 | | | | | | 60 |

| | | | | | | | | | | | | | | |
|---|---|---|---|---|---|---|---|---|---|---|---|---|---|---|
| Val | Phe | Gly | Val | Phe 65 | Leu | Leu | Trp | Phe 70 | Phe | Gln | Ala | Leu | Phe 75 | |
| Tyr | Leu | Leu | Pro | Ile 80 | Gly | Lys | Val | Val 85 | Glu | Gly | Leu | Pro | Leu | Ser 90 |
| Asn | Pro | Arg | Lys | Pro 95 | Gln | Tyr | Arg | Ile 100 | Asn | Gly | Phe | Tyr | Ala | Phe 105 |
| Leu | Leu | Thr | Ala | Ala 110 | Ala | Ile | Gln | Thr 115 | Leu | Leu | Tyr | Phe | Gln | Phe 120 |
| Glu | Leu | His | Tyr | Leu 125 | Tyr | Asp | His | Phe 130 | Val | Gln | Phe | Ala | Val | Ser 135 |
| Ala | Ala | Ala | Phe | Ser 140 | Met | Ala | Leu | Ser 145 | Ile | Tyr | Leu | Tyr | Ile | Arg 150 |
| Ser | Leu | Lys | Ala | Pro 155 | Glu | Glu | Asp | Leu 160 | Ala | Pro | Gly | Gly | Asn | Ser 165 |
| Gly | Tyr | Leu | Val | Tyr 170 | Asn | Phe | Phe | Thr 175 | Gly | His | Glu | Leu | Asn | Pro 180 |
| Arg | Ile | Gly | Ser | Phe 185 | Asp | Leu | Lys | Tyr 190 | Phe | Cys | Glu | Leu | Arg | Pro 195 |
| Gly | Leu | Ile | Gly | Trp 200 | Val | Val | Ile | Asn 205 | Leu | Ala | Met | Leu | Leu | Ala 210 |
| Glu | Met | Lys | Ile | His 215 | Asn | Gln | Ser | Met 220 | Pro | Ser | Leu | Ser | Met | Ile 225 |
| Leu | Val | Asn | Ser | Phe 230 | Gln | Leu | Leu | Tyr 235 | Val | Val | Asp | Ala | Leu | Trp 240 |
| Asn | Glu | Glu | Ala | Val 245 | Leu | Thr | Thr | Met 250 | Asp | Ile | Thr | His | Asp | Gly 255 |
| Phe | Gly | Phe | Met | Leu 260 | Ala | Phe | Gly | Asp 265 | Leu | Val | Trp | Val | Pro | Phe 270 |
| Val | Tyr | Ser | Leu | Gln 275 | Ala | Phe | Tyr | Ile 280 | Val | Gly | His | Pro | Ile | Ala 285 |
| Ile | Ser | Trp | Pro | Val 290 | Ala | Ala | Ala | Ile 295 | Thr | Ile | Leu | Asn | Cys | Ile 300 |
| Gly | Tyr | Tyr | Ile | Phe 305 | Arg | Ser | Ala | Asn 310 | Ser | Gln | Lys | Asn | Asn | Phe 315 |
| Arg | Arg | Asn | Pro | Ala 320 | Asp | Pro | Lys | Leu 325 | Ser | Tyr | Leu | Lys | Val | Ile 330 |
| Pro | Thr | Ala | Thr | Gly 335 | Lys | Gly | Leu | Leu 340 | Val | Thr | Gly | Trp | Trp | Gly 345 |
| Phe | Val | Arg | His | Pro 350 | Asn | Tyr | Leu | Gly 355 | Asp | Ile | Ile | Met | Ala | Leu 360 |
| Ala | Trp | Ser | Leu | Pro 365 | Cys | Gly | Phe | Asn 370 | His | Ile | Leu | Pro | Tyr | Phe 375 |
| Tyr | Val | Ile | Tyr | Phe 380 | Ile | Cys | Leu | Leu 385 | Val | His | Arg | Glu | Ala | Arg 390 |
| Asp | Glu | His | His | Cys 395 | Lys | Lys | Lys | Tyr 400 | Gly | Leu | Ala | Trp | Glu | Arg 405 |
| Tyr | Cys | Gln | Arg | Val 410 | Pro | Tyr | Thr | His 415 | Ile | Ser | Leu | His | Leu | |

( 2 ) INFORMATION FOR SEQ ID NO:3:

( i ) SEQUENCE CHARACTERISTICS:
        ( A ) LENGTH: 473 residues
        ( B ) TYPE: amino acid
        ( C ) STRANDEDNESS: single (D) TOPOLOGY: linear (ii) MOLECULE TYPE:
(A) DESCRIPTION: polypeptide (ix) FEATURE:
(A) NAME/KEY: *Saccharomyces cerevisiae* YGL022

(x) PUBLICATION INFORMATION:
(A) AUTHORS: W. Chen, E. Capieaux, E. Balzi, and A. Goffeau
(B) TITLE: The YGL022 Gene Encodes a Putative Transport Protein
(C) JOURNAL: Yeast
(D) VOLUME: 7
(F) PAGES: 305-308
Sequence set out in Figure 1, pages 306-307
(G) DATE: 1991
(K) RELEVANT RESIDUES IN SEQ ID NO: open reading frame (xi) SEQUENCE DESCRIPTION: SEQ ID NO: 3:

| Met | Ala | Lys | Asp | Asn | Ser | Glu | Lys | Leu | Gln | Val | Gln | Gly | Glu | Glu |
|---|---|---|---|---|---|---|---|---|---|---|---|---|---|---|
| | | | | 5 | | | | | 10 | | | | | 15 |
| Lys | Lys | Ser | Lys | Gln | Pro | Val | Asn | Phe | Leu | Pro | Gln | Gly | Lys | Trp |
| | | | | 20 | | | | | 25 | | | | | 30 |
| Leu | Lys | Pro | Asn | Glu | Ile | Glu | Tyr | Glu | Phe | Gly | Gly | Thr | Thr | Gly |
| | | | | 35 | | | | | 40 | | | | | 45 |
| Val | Ile | Gly | Met | Leu | Ile | Gly | Phe | Pro | Leu | Leu | Met | Tyr | Tyr | Met |
| | | | | 50 | | | | | 55 | | | | | 60 |
| Trp | Ile | Cys | Ala | Glu | Phe | Tyr | His | Gly | Lys | Val | Ala | Leu | Pro | Lys |
| | | | | 65 | | | | | 70 | | | | | 75 |
| Ala | Gly | Glu | Ser | Trp | Met | His | Phe | Ile | Lys | His | Leu | Tyr | Gln | Leu |
| | | | | 80 | | | | | 85 | | | | | 90 |
| Val | Leu | Glu | Asn | Gly | Ile | Pro | Glu | Lys | Tyr | Asp | Trp | Thr | Ile | Phe |
| | | | | 95 | | | | | 100 | | | | | 105 |
| Leu | Thr | Phe | Trp | Val | Phe | Gln | Ile | Ile | Phe | Tyr | Tyr | Thr | Leu | Pro |
| | | | | 110 | | | | | 115 | | | | | 120 |
| Gly | Ile | Trp | Thr | Lys | Gly | Gln | Pro | Leu | Ser | His | Leu | Lys | Gly | Lys |
| | | | | 125 | | | | | 130 | | | | | 135 |
| Gln | Leu | Pro | Tyr | Phe | Cys | Asn | Ala | Met | Trp | Thr | Leu | Tyr | Val | Thr |
| | | | | 140 | | | | | 145 | | | | | 150 |
| Thr | Thr | Leu | Val | Leu | Val | Leu | His | Phe | Thr | Asn | Leu | Phe | Arg | Leu |
| | | | | 155 | | | | | 160 | | | | | 165 |
| Tyr | Val | Ile | Ile | Asp | Arg | Phe | Gly | Arg | Ile | Met | Thr | Cys | Ala | Ile |
| | | | | 170 | | | | | 175 | | | | | 180 |
| Ile | Ser | Gly | Phe | Ala | Phe | Ser | Ile | Ile | Leu | Tyr | Leu | Trp | Thr | Leu |
| | | | | 185 | | | | | 190 | | | | | 195 |
| Phe | Ile | Ser | His | Asp | Tyr | His | Arg | Met | Thr | Gly | Asn | His | Leu | Tyr |
| | | | | 200 | | | | | 205 | | | | | 210 |
| Asp | Phe | Phe | Met | Gly | Ala | Pro | Leu | Asn | Pro | Arg | Trp | Gly | Ile | Leu |
| | | | | 215 | | | | | 220 | | | | | 225 |
| Asp | Leu | Lys | Met | Phe | Phe | Glu | Val | Arg | Leu | Pro | Trp | Phe | Thr | Leu |
| | | | | 230 | | | | | 235 | | | | | 240 |
| Tyr | Phe | Ile | Thr | Leu | Gly | Ala | Cys | Leu | Lys | Gln | Trp | Glu | Thr | Tyr |
| | | | | 245 | | | | | 250 | | | | | 255 |
| Gly | Tyr | Val | Thr | Pro | Gln | Leu | Gly | Val | Val | Met | Leu | Ala | His | Trp |
| | | | | 260 | | | | | 265 | | | | | 270 |
| Leu | Tyr | Ala | Asn | Ala | Cys | Ala | Lys | Gly | Glu | Glu | Leu | Ile | Val | Pro |
| | | | | 275 | | | | | 280 | | | | | 285 |
| Thr | Trp | Asp | Met | Ala | Tyr | Glu | Lys | Phe | Gly | Phe | Met | Leu | Ile | Phe |

|     |     |     |     | 290 |     |     |     | 295 |     |     |     | 300 |
|---|---|---|---|---|---|---|---|---|---|---|---|---|

Trp Asn Ile Ala Gly Val Pro Tyr Thr Tyr Cys His Cys Thr Leu
                    305                 310                 315

Tyr Leu Tyr Tyr His Asp Pro Ser Glu Tyr His Trp Ser Thr Leu
                    320                 325                 330

Tyr Asn Val Ser Leu Tyr Val Val Leu Leu Cys Ala Tyr Tyr Phe
                    335                 340                 345

Phe Asp Thr Ala Asn Ala Gln Lys Asn Ala Phe Arg Lys Gln Met
                    350                 355                 360

Ser Gly Asp Lys Thr Val Arg Lys Thr Phe Pro Phe Leu Pro Tyr
                    365                 370                 375

Gln Ile Leu Lys Asn Pro Lys Tyr Met Val Thr Ser Asn Gly Ser
                    380                 385                 390

Tyr Leu Leu Ile Asp Gly Trp Tyr Thr Leu Ala Arg Lys Ile His
                    395                 400                 405

Tyr Thr Ala Asp Trp Thr Gln Ser Leu Val Trp Ala Leu Ser Cys
                    410                 415                 420

Gly Phe Asn Ser Val Phe Pro Trp Phe Phe Pro Val Phe Phe Leu
                    425                 430                 435

Val Val Leu Ile His Arg Ala Phe Arg Asp Gln Ala Lys Cys Lys
                    440                 445                 450

Arg Lys Tyr Gly Lys Asp Trp Asp Glu Tyr Cys Lys His Cys Pro
                    455                 460                 465

Tyr Val Phe Ile Pro Tyr Val Phe
                    470

( 2 ) INFORMATION FOR SEQ ID NO:4:

( i ) SEQUENCE CHARACTERISTICS:
        ( A ) LENGTH: 453 residues
        ( B ) TYPE: amino acid
        ( C ) STRANDEDNESS: single
        ( D ) TOPOLOGY: linear ( i i ) MOLECULE TYPE:
        ( A ) DESCRIPTION: polypeptide ( i x ) FEATURE:
        ( A ) NAME/KEY: *Schizosaccharomyces pombe sts gene*

( x ) PUBLICATION INFORMATION:
        ( A ) AUTHORS: M. Shimanuki, M. Goebl, M. Yanagida, and T. Toda
        ( B ) TITLE: Fission Yeast sts1+Gene Encodes a Protein Similar to the Chicken Lamin B Receptor
        ( C ) JOURNAL: *Molecular Biology of the Cell*
        ( D ) VOLUME: 3
        ( F ) PAGES: 263-273
            Sequence set out in Figure 1, page 264
        ( G ) DATE: 1992
        ( K ) RELEVANT RESIDUES IN SEQ ID NO: open reading frame ( x i ) SEQUENCE DESCRIPTION: SEQ ID NO: 4:

Met Lys Ser Thr Val Lys Lys Ser Ala Pro Arg Glu Phe Gly Gly
                    5                   10                  15

Ala Lys Gly Ala Leu Ala Ile Met Thr Gly Phe Pro Cys Leu Met
                    20                  25                  30

Tyr Tyr Leu Trp Ala Cys Ser Lys Phe Asn Asp Ser Gln Phe Ile
                    35                  40                  45

Lys Pro Glu Ser Phe Thr Ile Ala Gly Phe Gln Asn Phe Phe Arg

|      |     |     |     |     | 50  |     |     |     |     | 55  |     |     |     |     | 60  |
|------|-----|-----|-----|-----|-----|-----|-----|-----|-----|-----|-----|-----|-----|-----|-----|
| Thr  | Leu | Gly | His | Tyr | Ile | Tyr | Val | Gly | Ala | Tyr | Pro | Thr | Arg | Tyr |     |
|      |     |     |     | 65  |     |     |     |     | 70  |     |     |     |     | 75  |     |
| Ala  | Phe | Leu | Val | Phe | Trp | Ser | Phe | Cys | Ile | Val | Gln | Ala | Val | Met |     |
|      |     |     |     | 80  |     |     |     |     | 85  |     |     |     |     | 90  |     |
| Tyr  | Leu | Thr | Leu | Pro | Gly | Val | Arg | Thr | Gln | Gly | Leu | Pro | Leu | Lys |     |
|      |     |     |     | 95  |     |     |     |     | 100 |     |     |     |     | 105 |     |
| His  | Arg | Asn | Asn | Glu | Arg | Leu | Pro | Tyr | Leu | Cys | Asn | Ala | Ile | Trp |     |
|      |     |     |     | 110 |     |     |     |     | 115 |     |     |     |     | 120 |     |
| Ser  | Phe | Tyr | Thr | Thr | Ile | Val | Ile | Leu | Ala | Val | Leu | His | Val | Thr |     |
|      |     |     |     | 125 |     |     |     |     | 130 |     |     |     |     | 135 |     |
| His  | Val | Phe | Pro | Ile | Thr | Thr | Phe | Ile | Asp | Met | Phe | Gly | Pro | Leu |     |
|      |     |     |     | 140 |     |     |     |     | 145 |     |     |     |     | 150 |     |
| Met  | Ser | Val | Ala | Ile | Ile | Thr | Ala | Phe | Val | Cys | Thr | Phe | Val | Leu |     |
|      |     |     |     | 155 |     |     |     |     | 160 |     |     |     |     | 165 |     |
| Tyr  | Thr | Gly | Thr | Leu | Leu | Phe | Gly | Asp | Arg | Leu | Phe | Asp | Lys | Pro |     |
|      |     |     |     | 170 |     |     |     |     | 175 |     |     |     |     | 180 |     |
| His  | Arg | Leu | Ser | Gly | Asn | Pro | Ile | Tyr | Asp | Ala | Phe | Met | Gly | Ala |     |
|      |     |     |     | 185 |     |     |     |     | 190 |     |     |     |     | 195 |     |
| Cys  | Leu | Asn | Pro | Arg | Leu | Gly | Lys | Leu | Leu | Asp | Phe | Lys | Met | Phe |     |
|      |     |     |     | 200 |     |     |     |     | 205 |     |     |     |     | 210 |     |
| Phe  | Glu | Val | Arg | Ile | Pro | Trp | Phe | Ile | Leu | Phe | Phe | Ile | Ser | Val |     |
|      |     |     |     | 215 |     |     |     |     | 220 |     |     |     |     | 225 |     |
| Gly  | Ala | Ala | Val | Arg | Gln | Tyr | Glu | Thr | Tyr | Gly | Thr | Val | Ser | Pro |     |
|      |     |     |     | 230 |     |     |     |     | 235 |     |     |     |     | 240 |     |
| Gln  | Val | Leu | Phe | Val | Cys | Leu | Gly | His | Tyr | Leu | Tyr | Ala | Asn | Ala |     |
|      |     |     |     | 245 |     |     |     |     | 250 |     |     |     |     | 255 |     |
| Cys  | Ser | Lys | Gly | Glu | Gln | Leu | Ile | Val | Pro | Thr | Trp | Asp | Met | Ala |     |
|      |     |     |     | 260 |     |     |     |     | 265 |     |     |     |     | 270 |     |
| Tyr  | Glu | Lys | Phe | Gly | Phe | Met | Leu | Ile | Phe | Trp | Asn | Met | Ala | Gly |     |
|      |     |     |     | 275 |     |     |     |     | 280 |     |     |     |     | 285 |     |
| Val  | Pro | Phe | Thr | Tyr | Ser | His | Cys | Thr | Leu | Tyr | Leu | Phe | Ser | His |     |
|      |     |     |     | 290 |     |     |     |     | 295 |     |     |     |     | 300 |     |
| Asp  | Pro | Ser | Val | Tyr | Asn | Trp | Ser | Thr | Gln | Tyr | Thr | Thr | Gly | Ile |     |
|      |     |     |     | 305 |     |     |     |     | 310 |     |     |     |     | 315 |     |
| Tyr  | Val | Leu | Leu | Leu | Cys | Cys | Tyr | Tyr | Ile | Phe | Asp | Thr | Cys | Asn |     |
|      |     |     |     | 320 |     |     |     |     | 325 |     |     |     |     | 330 |     |
| Gly  | Gln | Lys | Asn | His | Phe | Arg | Asn | Gln | Ile | Tyr | Gly | Thr | Glu | Val |     |
|      |     |     |     | 335 |     |     |     |     | 340 |     |     |     |     | 345 |     |
| His  | Arg | Lys | Thr | Phe | Pro | Gln | Leu | Pro | Trp | Leu | Ile | Ile | Lys | Asn |     |
|      |     |     |     | 350 |     |     |     |     | 355 |     |     |     |     | 360 |     |
| Pro  | Thr | Phe | Ile | Arg | Cys | Ala | Asn | Gly | Gly | Thr | Leu | Leu | Thr | Ser |     |
|      |     |     |     | 365 |     |     |     |     | 370 |     |     |     |     | 375 |     |
| Gly  | Trp | Tyr | Arg | Tyr | Ala | Arg | Lys | Ile | His | Tyr | Thr | Ala | Asp | Phe |     |
|      |     |     |     | 380 |     |     |     |     | 385 |     |     |     |     | 390 |     |
| Phe  | Gln | Ser | Leu | Ser | Trp | Ala | Leu | Ile | Thr | Gly | Phe | Gln | Ser | Pro |     |
|      |     |     |     | 395 |     |     |     |     | 400 |     |     |     |     | 405 |     |
| Leu  | Pro | Tyr | Phe | Tyr | Pro | Ser | Phe | Phe | Phe | Val | Val | Leu | Val | His |     |
|      |     |     |     | 410 |     |     |     |     | 415 |     |     |     |     | 420 |     |
| Arg  | Val | Ser | Arg | Asp | Ile | Lys | Lys | Cys | Lys | Ala | Lys | Tyr | Gly | Ala |     |
|      |     |     |     | 425 |     |     |     |     | 430 |     |     |     |     | 435 |     |
| Asp  | Phe | Asp | Glu | Tyr | Asp | Arg | Ile | Cys | Pro | Tyr | Leu | Phe | Ile | Pro |     |
|      |     |     |     | 440 |     |     |     |     | 445 |     |     |     |     | 450 |     |

Tyr Ile Phe (2) INFORMATION FOR SEQ ID NO:5:

(i) SEQUENCE CHARACTERISTICS:
        (A) LENGTH: 438 amino acids
        (B) TYPE: amino acid
        (C) STRANDEDNESS: single
        (D) TOPOLOGY: linear (ii) MOLECULE TYPE:
        (A) DESCRIPTION: polypeptide (v) FRAGMENT TYPE: entire sequence (vi) IMMEDIATE SOURCE: *Saccharomyces cerevisiae*
        clone (ix) FEATURE:
        (D) OTHER INFORMATION: translated polypeptide of
        sterol [0081]14
        reductase gene (xi) SEQUENCE DESCRIPTION: SEQ ID NO: 5:

```
Met Val Ser Ala Leu Asn Pro Arg Thr Thr Glu Phe Glu Phe Gly
                 5                  10                  15

Gly Leu Ile Gly Ala Leu Gly Ile Ser Ile Gly Leu Pro Val Phe
                20                  25                  30

Thr Ile Ile Leu Asn Gln Met Ile Arg Pro Asp Tyr Phe Ile Lys
                35                  40                  45

Gly Phe Phe Gln Asn Phe Asp Ile Val Glu Leu Trp Asn Gly Ile
                50                  55                  60

Lys Pro Leu Arg Tyr Tyr Leu Gly Asn Arg Glu Leu Trp Thr Val
                65                  70                  75

Tyr Cys Leu Trp Tyr Gly Ile Leu Ala Val Leu Asp Val Ile Leu
                80                  85                  90

Pro Gly Arg Val Met Lys Gly Val Gln Leu Arg Asp Gly Ser Lys
                95                  100                 105

Leu Ser Tyr Lys Ile Asn Gly Ile Ala Met Ser Thr Thr Leu Val
                110                 115                 120

Leu Val Leu Ala Ile Arg Trp Lys Leu Thr Asp Gly Gln Leu Pro
                125                 130                 135

Glu Leu Gln Tyr Leu Tyr Glu Asn His Val Ser Leu Cys Ile Ile
                140                 145                 150

Ser Ile Leu Phe Ser Phe Phe Leu Ala Thr Tyr Cys Tyr Val Ala
                155                 160                 165

Ser Phe Ile Pro Leu Ile Phe Lys Lys Asn Gly Asn Gly Lys Arg
                170                 175                 180

Glu Lys Ile Leu Ala Leu Gly Gly Asn Ser Gly Asn Ile Ile Tyr
                185                 190                 195

Asp Trp Phe Ile Gly Arg Glu Leu Asn Pro Arg Leu Gly Pro Leu
                200                 205                 215

Asp Ile Lys Met Phe Ser Glu Leu Arg Pro Gly Met Leu Leu Trp
                215                 220                 225

Leu Leu Ile Asn Leu Ser Cys Leu His His His Tyr Leu Lys Thr
                230                 235                 240

Gly Lys Ile Asn Asp Ala Leu Val Leu Val Asn Phe Ser Gln Gly
                245                 250                 255

Phe Tyr Ile Phe Asp Gly Val Leu Asn Glu Gly Val Leu Thr
                260                 265                 270
```

| | | | | | | | | | | | | | |
|---|---|---|---|---|---|---|---|---|---|---|---|---|---|
| Met | Met | Asp | Ile | Thr 275 | Thr | Asp | Gly | Phe | Gly 280 | Phe | Met | Leu | Ala | Phe 285 |
| Gly | Asp | Leu | Ser | Leu 290 | Val | Pro | Phe | Thr | Tyr 295 | Ser | Leu | Gln | Ala | Arg 300 |
| Tyr | Leu | Ser | Val | Ser 305 | Pro | Val | Glu | Leu | Gly 310 | Trp | Val | Lys | Val | Val 315 |
| Gly | Ile | Leu | Ala | Ile 320 | Met | Phe | Leu | Gly | Phe 325 | His | Ile | Phe | His | Ser 330 |
| Ala | Asn | Lys | Gln | Lys 335 | Ser | Glu | Phe | Arg | Gln 340 | Gly | Lys | Leu | Glu | Asn 345 |
| Leu | Lys | Ser | Ile | Gln 350 | Thr | Lys | Arg | Gly | Thr 355 | Lys | Leu | Leu | Cys | Asp 360 |
| Gly | Trp | Trp | Ala | Lys 365 | Ser | Gln | His | Ile | Asn 370 | Tyr | Phe | Gly | Asp | Trp 375 |
| Leu | Ile | Ser | Leu | Ser 380 | Trp | Cys | Leu | Ala | Thr 385 | Trp | Phe | Gln | Thr | Pro 390 |
| Leu | Thr | Tyr | Tyr | Tyr 395 | Ser | Leu | Tyr | Phe | Ala 400 | Thr | Leu | Leu | Leu | His 405 |
| Arg | Gln | Gln | Arg | Asp 410 | Glu | His | Lys | Cys | Arg 415 | Leu | Lys | Tyr | Gly | Glu 420 |
| Asn | Trp | Glu | Glu | Tyr 425 | Glu | Arg | Lys | Val | Pro 430 | Tyr | Lys | Ile | Ile | Pro 435 |
| Tyr | Val | Tyr | | | | | | | | | | | | |